United States Patent [19]

Kesseler et al.

[11] Patent Number: 5,401,498
[45] Date of Patent: Mar. 28, 1995

[54] PHARMACEUTICALS COMPRISING POLYHYDROXYMETHYLENE DERIVATIVES, PROCESS FOR THEIR PREPARATION AND USE

[75] Inventors: Kurt Kesseler, Bad Soden am Taunus; Rudolf Schmidtberger, Marburg; Stefan Müllner, Hochheim am Main; Ernold Granzer, Kelkheim, all of Germany

[73] Assignee: Hoechst Aktiengesellschaft, Frankfurt am Main, Germany

[21] Appl. No.: 37,125

[22] Filed: Mar. 25, 1993

[30] Foreign Application Priority Data

Mar. 28, 1992 [DE] Germany ............ 42 10 220.0

[51] Int. Cl.⁶ ............... A61K 31/765; A61K 31/785
[52] U.S. Cl. ............... 424/78.11; 424/78.1; 424/78.32; 424/78.22
[58] Field of Search ............ 424/78.32, 78.22, 78.01, 424/78.1, 78.11, 78.36, 78.37

[56] References Cited

U.S. PATENT DOCUMENTS

| | | | |
|---|---|---|---|
| 3,980,770 | 9/1976 | Ingelman et al. | 424/78.1 |
| 4,027,009 | 5/1977 | Grier et al. | 424/78.1 |
| 4,098,771 | 7/1978 | Huemer et al. | 526/209 |
| 4,565,652 | 1/1986 | Schmidtberger | 424/101 |

FOREIGN PATENT DOCUMENTS 584078 10/1985 Australia .

*Primary Examiner*—Thurman K. Page
*Assistant Examiner*—Peter F. Kulkosky
*Attorney, Agent, or Firm*—Finnegan, Henderson, Farabow, Garrett & Dunner

[57] ABSTRACT

The invention relates to a pharmaceutical containing an effective amount of a polyhydroxymethylene containing grafted ethoxylated alcohols and/or ethoxylated carboxylic acids.

The pharmaceutical is used for the treatment of dyslipoproteinemias.

20 Claims, No Drawings

PHARMACEUTICALS COMPRISING POLYHYDROXYMETHYLENE DERIVATIVES, PROCESS FOR THEIR PREPARATION AND USE

The invention relates to pharmaceuticals containing polyhydroxymethylene derivatives and to their use for the treatment of dyslipoproteinemias.

At present, various strategies are used for the treatment of dyslipoproteinemias, depending on the nature and severity of the clinical picture, the patient history and the effects of other risk factors. As a result of the development and market introduction of HMG-CoA reductase inhibitors, it has recently been possible to intervene specifically in cholesterol biosynthesis, in particular in cholesterol biosynthesis in the liver, in order in this way effectively to decrease the plasma cholesterol level. The hypolipidemic agents already on the market for some time, such as, for example, bile acid sequestrants (colestyramine), antioxidants (probucol), fibrates (bezafibrate, clofibrate), nicotinic acid and derivatives (acipimox), neomycin and plant sterols (sitosterol), hormones and omega-3-fatty acids have thus admittedly not become completely unimportant, but since then only have importance for special indications.

A disadvantage with most of the hypolipidemic agents mentioned are their in some cases substantial side effects, so that their use in some cases can only be justified in reinfarct prophylaxis and in inherited dyslipoproteinemia. According to the results of the large-scale clinical studies of recent years, for example the Framingham Study and Helsinki Heart Study, it was necessary to intervene medicinally substantially earlier in the case of elevated cholesterol values, in particular in young people and people of middle age, in order to act effectively against the No. 1 cause of death in the western world, atherosclerosis. However, this immediately leads to problems of acceptance with the patients who, because they do not feel ill, cannot recognize the risk and are thus also not ready to accept side effects, where simultaneously no noticeable effect becomes apparent. On the other hand, strict dietetic measures with mediocre effectiveness often mean far more substantial restrictions for the patients than the burden of known side effects.

The present invention is based on the object, in accordance with the desire of the treating physicians, of making available a hypolipidemic agent, which
1. shows no side effects or only slight side effects on long-term use,
2. is distinguished by high palatability and is available in a formulation which is ideal for the patient, for example a tablet, capsule, coated tablet or the like, and
3. effectively and efficiently decreases the plasma cholesterol level.

Ideally, these should be non-systemically acting pharmaceuticals which have to be constituted such that they survive the intestinal passage in a non-absorbable and non-degradable manner.

Additionally, as in all pharmaceuticals, a toxicological acceptability must be imparted.

Said requirements are surprisingly fulfilled by a pharmaceutical which contains at least one polyhydroxymethylene containing grafted ethoxylated alcohols and/or ethoxylated carboxylic acids.

The invention therefore relates to a pharmaceutical comprising an effective content of a polyhydroxymethylene containing grafted ethoxylated alcohols and/or ethoxylated carboxylic acids.

The polyhydroxymethylene containing grafted ethoxylated alcohols and/or ethoxylated carboxylic acids is a polymer, essentially containing units (I) and/or (II) as constituents of the base polymer

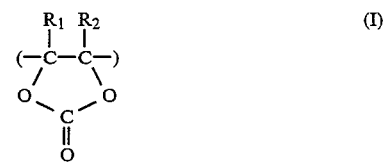

in which $R_1$ and $R_2$ independently of one another are hydrogen or a monovalent hydrocarbon radical having up to 8 carbon atoms, and optionally small amounts of further monomer units, the base polymer additionally keeping units covalently bound which are derived from at least one compound of the formula (III)

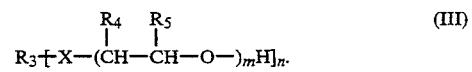

in which the symbols $R_3$, X, $R_4$, $R_5$, m and n have the following meaning:

$R_3$ is a hydrocarbon radical having 4 to 30 carbon atoms, preferably an alkyl radical having 4 to 30 carbon atoms, preferably having 12 to 20 carbon atoms, or an aryl radical having 6 to 14 carbon atoms, preferably having 6 to 10 carbon atoms, preferably a phenyl radical, it optionally being possible for this aryl (phenyl) radical to be substituted by one, preferably 1 to 3 alkyl radicals having 4 to 30 carbon atoms, preferably 12 to 20 carbon atoms;

X is —O—, —NH— and/or —COO—, preferably —COO— and/or —O—;

$R_4$ and $R_5$ independently of one another are hydrogen or a monovalent hydrocarbon radical, in particular an alkyl radical having 1 to 8 carbon atoms, with the proviso that at least one of the radicals $R_4$ and $R_5$ is hydrogen;

m is an integer from 1 to 40, preferably 5 to 35;

n is an integer from 1 to 4, preferably 1 or 2.

The base polymer of the polymer consists essentially, preferably up to at least 90% by weight, of the above units (I) and/or (II), $R_1$ and $R_2$ preferably denote an alkyl radical having 1 to 6 carbon atoms and in particular one having 1 to 4 carbon atoms. Examples of these are: the methyl, ethyl, isopropyl, 2-ethylhexyl, n-heptyl, cyclopentyl, phenyl, tolyl, benzyl or xylyl radical.

The radicals $R_1$ and $R_2$ are particularly preferably hydrogen.

According to a further preferred embodiment of the invention, the amount of units (II) is more than 50% by weight, relative to the total amount of (I) and (II), i.e. the majority of the cyclocarbonate groups of (I) are hydrolyzed to hydroxy groups. In particular, the amount of (II) is at least 95% by weight and particularly preferably 100% by weight.

The base polymer can optionally also contain small amounts of other monomer units which are derived from monomers and which are copolymerizable with vinylene carbonate or its derivatives. These monomers can also have hydrophilic or crosslinking groups. Examples of monomers of this type which may be mentioned here are: vinylpyrrolidone, alkyl(meth)acrylates each having 2 to 6 carbon atoms in the alkyl group, hydroxyalkyl esters of (meth)acrylic acid having 2 to 6 carbon atoms in the alkyl group, N-vinyl-N-alkylacetamide ($C_1$–$C_4$-alkyl), vinyl acetate, divinyl ethers of glycols such as ethylene glycol divinyl ether, butanediol divinyl ether, hexanediol divinyl ether, N,N'-alkylenebis(meth)acrylamides having straight-chain or branched alkylene radicals containing up to 12 carbon atoms, preferably up to 6 carbon atoms, such as N,N'-methylenebisacrylamide, N,N'-ethylenebisacrylamide, N,N'-hexamethylenebisacrylamide, N,N'-ethylidenebisacrylamide, glyoxalbisacrylamide (1,2-bisacrylamido-1,2-dihydroxyethane), bisacrylamidoacetic acid, ethylene glycol bis-methacrylic acid-glycol bis-methacrylic acid ester, butanediolbismethacrylic acid ester, triallyl cyanurate, trisacryloylperhydrotriazine, divinylbenzene, divinyl adipate, N,N'-divinylethyleneurea, N,N'-divinylpropyleneurea, ethylidenebis-3-(N-vinylpyrrolidone), N,N'-2,2'-divinyldiimidazolyl and 1,1'-bis(3,3'-vinylbenzimidazolid-2-one)-1,4-butane, vinyl acrylate, allyl methacrylate, acrylic and methacrylic acid esters having 5 to 12 carbon atoms in the alkyl radical, (meth)acrylonitrile, vinyl esters having 4 to 18 carbon atoms in the carboxylic acid radical, such as vinyl butyrate, vinyl stearate, and vinyl esters of branched carboxylic acids having 10 to 12 carbon atoms; furthermore vinylaromatics, such as styrene or α-methylstyrene.

A plurality of units derived from these monomers can also be present in the base polymer.

The quantity of these monomer units, if present, in general does not exceed 15% by weight and is preferably at most 10% by weight, in each case relative to the total base polymer.

The base polymer, however, preferably consists only of the units (I) and/or (II).

The base polymer contains units which are derived from at least one compound of the formula (III). These units can in this case also derive from various compounds of the formula (III), i.e. mixtures of the various compounds according to formula (III) can also be used in the preparation of the polymers according to the invention.

The quantity of these units according to (III) is as a rule up to 30% by weight, preferably 1 to 20% by weight, and in particular 7 to 15% by weight, in each case relative to the base polymer.

In the above formula (III), the individual substituents are preferably the following:

$R_3$ is a branched, but preferably unbranched, alkyl radical having 4 to 30 carbon atoms, preferably 12 to 20 carbon atoms. Examples which may be mentioned are: hexyl, heptyl, octyl, nonyl, decyl, undecyl, dodecyl, hexadecyl, octadecyl, eicosyl.

X is —O—; —NH— and/or —COO—; in particular —O—;

$R_4$ and $R_5$ are hydrogen or methyl, in particular hydrogen;

m is an integer from 5 to 35;

n is 1 or 2, in particular 1.

Preferred representatives of the formula (III) are accordingly ethoxylated, monobasic aliphatic carboxylic acids (($C_4$–$C_{30}$)-alkyl), mixtures of acids of this type (for example fatty acids) also being suitable. Particularly preferred representatives which can be mentioned here are ethoxylated, monovalent aliphatic alcohols (($C_4$–$C_{30}$)-alkyl), which are preferably primary. Mixtures of alcohols of this type (for example fatty alcohols) can also be used here.

Possible representatives of the formula (III) are, for example, also ethoxylated, monovalent, in particular primary, amines (X=—NH—), ethoxylated hydroxycarboxylic acids (X=—O— and —COO—, n=2), ethoxylated aromatic carboxylic acids ($R_3$=phenyl) or polyhydric/polybasic alcohols/carboxylic acids (n>1).

Polyhydroxymethylenes are therefore preferred, in each case containing units of ethoxylated, monobasic aliphatic carboxylic acids (($C_4$–$C_3$)-alkyl) or in particular ethoxylated, monohydric aliphatic alcohols (($C_4$–$C_3$)-alkyl) in preferred amounts from 1 to 20% by weight, in particular from 7 to 15% by weight.

The base polymer and the units derived from the compounds according to formula (III) are linked to one another by covalent bonds. In this case, the majority of the units incorporated in the polymer, derived from the compounds according to formula (III), should be grafted onto the base polymer. In addition, incorporation as end groups is also conceivable. In the case of relatively large numerical values for m, i.e. in the case of relatively long polyether radicals, grafting of polyvinylene carbonate chains to the alkoxylated compounds according to formula (III) can also occur.

The preparation of these compounds is described in DE-A-3,413,904 and in counterpart U.S. Pat. Nos. 4,788,278; 4,839,439; and 4,906,570.

The action of the polyhydroxymethylene derivatives described comprises the adsorption of dietetic cholesterol and the inhibition of absorption resulting therefrom. This inhibition leads to a noticeable decrease in the serum cholesterol level. Since the medicament itself is not absorbable, it is also not to be expected that side effects will occur as with the systemically active hypolipidemic agent. A further advantage of the polyhydroxymethylene derivatives is their absolute flavor and odor neutrality and their pleasant consistency, on account of which no additives whatsoever have to be used for the formulation of preparations which increase patient compliance.

The proposed dose of the polyhydroxymethylene derivatives used according to the invention is, according to the animal experimental results data, in the range from 50 mg to 5 g per day, relative to 1 kg of body weight, preferably in doses of 75 mg to 1000 mg, particularly preferably in doses of 100 mg to 500 mg and very particularly preferably in doses of 125 mg to 300 mg.

A further surprising result is that a combination of said polyhydroxymethylene derivatives with other bile acid sequestrants, such as, for example colestyramine or colestipol or in particular with uncrosslinked or crosslinked alkylated polyethyleneimine derivatives and with other hypolipidemic agents such as fibrates, probucol, sitosterin, nicotinic acid (derivatives) or HMG-CoA reductase inhibitors is possible and the use of this combination with at least constant or even increased action permits a dose reduction with the polyhydroxymethylene derivatives.

The invention therefore also relates to a pharmaceutical containing an effective combination of at least one polyhydroxymethylene having grafted ethoxylated alcohols and/or ethoxylated carboxylic acids of the formula (I) to (III) and at least one uncrosslinked or crosslinked alkylated polyethyleneimine derivative, another bile acid sequestrant, for example colestyramine or colestipol or another hypolipidemic agent, for example fibrate, probucol, sitosterin, a nicotinic acid (derivative) or an HMG-CoA reductase inhibitor or with several of the abovementioned polyethyleneimine derivatives and/or several other bile acid sequestrants and/or other hypolipidemic agents.

The preparation of the polyethyleneimine derivatives used according to the invention is described in DE-A-3,901,527 and German Patent Applications P 41 31 507.3 and P 41 31 506.5. The other bile acid sequestrants or hypolipidemic agents mentioned are commercially available.

The uncrosslinked and crosslinked alkylated polyethyleneimines are characterized by the fact that the starting polyethyleneimine has a molecular weight of 10,000 to 10,000,000 and the alkylating agent has the formula (IV)

R—X  (IV)

in which
X is chlorine, bromine, iodine, $CH_3$—$SO_2$—O or

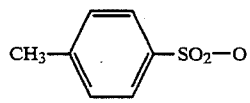

and
R is a straight-chain, branched or cyclic $C_1$ to $C_{30}$-alkyl radical, which is optionally substituted by a mono- or bicyclic saturated hydrocarbon having 5 to 10 ring carbon atoms or by a phenyl radical, and which in the case of a crosslinked alkylated polyethyleneimine contains as a crosslinking agent an $\alpha,\omega$-dihaloalkane having 2 to 10 carbon atoms or a more highly functionalized haloalkane having 2 to 10 carbon atoms.

In the alkylating agent, R—X is preferably chlorine or bromine. If R is a straight-chain radical, a primary alkyl radical is preferred.

The straight-chain or branched $C_1$ to $C_{30}$-alkyl radicals are preferably substituted by said ring systems. Preferably, the substituents are linked with the polyethyleneimine via spacers having 1 to 4 $CH_2$ groups. The cyclohexyl radical, in particular, is suitable as a monocyclic saturated substituent. A suitable bicyclic hydrocarbon radical is, for example, decalin. A particularly suitable alkylating agent whose alkyl radical is substituted by phenyl is benzyl bromide. A possible alkylating agent having a straight-chain alkyl radical is preferably butyl chloride.

If the radicals R are straight-chain or branched, both crosslinked and uncrosslinked polyethyleneimines are preferred.

If R in formula (IV) is a cyclic $C_5$ to $C_{30}$-alkyl radical, this can be monocyclic, bicyclic, tricyclic or polycyclic, optionally also bridged.

Generally preferred are uncrosslinked cyclic polyethyleneimines, in particular those in which R is cyclopentyl, cyclohexyl, cycloheptyl, cyclooctyl, cyclononyl, cyclodecyl, a bicyclic radical such as decalyl, hydrindanoyl, a bridged radical such as norbornyl, or a polycyclic radical such as cyclopentanoperhydrophenanthrene and a ring system or derivative derived therefrom.

According to the invention, polyethyleneimines having a molecular weight above 100,000 are preferably employed.

The alkylation as such can be carried out in several substeps. As a result of this, the possibility exists of fixing various substituents to the same polymer.

The ratio of the alkylating agent employed to the amino groups of the polyethyleneimine is 0.2:1 to 5:1, preferably 0.5:1 to 2:1. As a result of the reaction with alkylating agent, some of the secondary amino groups of the chain are converted into tertiary and quaternary structures. The formation of tertiary amino groups is preferred.

Suitable crosslinking agents are, for example, di- and trihaloalkanes, preferably $\alpha,\omega$-dihaloalkanes such as, for example, 1,6-dibromohexane and 1,10-dibromodecane. The amount of crosslinking agent is preferably 2 to 25 mol %, relative to the alkylating agent employed.

Using bio-inert excipients, such as active carbon, cellulose, chitosan, cyclodextrins, polyvinylpyrrolidone, polyvinyl alcohol or polyacrylic acid(s) derivatives, for example ®Carbopol, and optionally other additives and/or auxiliaries, the pharmaceuticals are brought into a suitable form for administration, such as tablets, capsules, coated tablets etc.

The pharmaceuticals according to the invention, containing a combination of at least one polyhydroxymethylene derivative and at least one other bile acid sequestrant or another hypolipidemic agent, but particularly preferably the combination of polyhydroxymethylene derivative(s) and polyethyleneimine derivative(s), show particularly advantageous properties, in particular in comparison with pharmaceuticals exclusively containing polyhydroxymethylene derivatives. Thus, the dose of the polyhydroxymethylene derivatives in combined use can be reduced with constant or improved activity compared with exclusive use.

According to the data from animal experimental results for the polyhydroxymethylene derivatives, the proposed doses for the constituents of the pharmaceutical according to the invention described above are in the range from 50 mg to 5 g, preferably 75 mg to 1,000 mg, particularly preferably 100 mg to 500 mg and very particularly preferably 125 mg to 300 mg per day, relative to 1 kg of body weight, and for the other bile acid sequestrants, in particular the polyethyleneimine derivatives, in the range from 10 mg to 10 g, preferably from 25 mg to 5 g, particularly preferably from 40 mg to 500 mg and very particularly preferably 50 mg per day, relative to 1 kg of body weight.

The therapeutic activity of the pharmaceutical according to the invention is demonstrated by the results of an animal experiment on rabbits.

Animal Experiment

Action of polyhydroxymethylene derivatives on the serum cholesterol concentration of hypercholesterolemic NZW rabbits:

Method

A moderate to severe hypercholesterolemia was produced in male NZW rabbits having an average starting value of the serum cholesterol of 25 mg/dl by a two-week administration of a feed enriched with 0.2% cholesterol. Three groups of 6 animals were assembled such that their average (increased) serum cholesterol content was about 61 to 69 mg/dl. Among the 6 animals, in each case 5 having moderate hypercholesterolemia (values between 30 and 51 mg/dl) and 1 animal having a severely increased serum cholesterol value were present. With further supply of the rabbit feed enriched with 0.2% cholesterol, they received polyhydroxymethylene-L (PHM-L; manufacturer: Riedel de Haen, item number 39 350) orally by stomach tube and the control received only the vehicle 1% ®Tylose MH 300 (methylhydroxycellulose; manufacturer: HOECHST AG).

The doses were 125 or 500 mg/kg of body weight/day of PHM-L, administered once daily. Altogether, 10 administrations were made, and the behavior of the serum cholesterol was also monitored in the immediately following omission phase (no further administration of PHM-L or Tylose ®, but further administration of cholesterol diet feed). The data are shown in Tables 1a and b. In addition to the absolute values (mg/dl of cholesterol), the mean percentage changes in the serum cholesterol for the 2 groups of PHM-L-treated animals are given compared to the control group (1% ®Tylose MH 300). It can thus be assessed what effect treatment with PHM-L in a dose- and time-dependent manner has and how the serum cholesterol concentration develops during the omission phase after the withdrawal of the PHM-L treatment.

Result

At doses of 125 or 500 mg/kg/day, it is possible to reduce the existing hypercholesterolemia of the rabbits and this is also continuous during the omission phase of up to 32 days. In an analogous earlier experiment, the dose of 250 mg/kg/day also had antihypercholesterolemic activity.

| | |
|---|---|
| Total experimental period: | 58 days |
| Change-over to cholesterol diet feed: | 1st day |
| First PHM-L administration: | 16th day |
| Last PHM-L administration: | 26th day |
| Last sampling/end of experiment: | 58th day |
| Animal species: | white male New Zealand rabbits |
| Strain: | NZB |
| Number of animals: | 18 (3 × 6) |
| Method of administration: | oral (stomach tube) |
| Vehicle: | 1% ®Tylose MH 300 |
| Number of administrations: | 10 |
| Type of feed: | 0.2% cholesterol diet based on commercially available feed meal |

TABLE 1a

| | | Serum cholesterol [mg/dl] | | | | | | |
|---|---|---|---|---|---|---|---|---|
| | | Starting values before start of administration of the preparation | | Values during the administration of the preparation | | Values after discontinuation of the preparation | | |
| Preparation (Dose) | Animal No. | 1st | 11th day of diet | 3rd | 8th day of administration | 4th | 12th | 32nd day of omission |
| Control | 1 | 26 | 32 | 34 | 34 | 39 | 27 | 80 |
| Tylose MH 300 | 2 | 24 | 32 | 48 | 43 | 38 | 32 | 168 |
| (1% strength) | 3 | 24 | 37 | 47 | 61 | 75 | 94 | — |
| | 4 | 26 | 40 | 43 | 47 | 28 | 25 | 104 |
| | 5 | 27 | 51 | 67 | 83 | 89 | 75 | 123 |
| | 6 | 36 | 221 | 350 | 364 | 464 | 406 | 601 |
| X | | 27 | 69 | 98 | 105 | 122 | 110 | 215 |
| S | | 4.5 | 74.8 | 124 | 128 | 169 | 148 | 218 |
| PEM-L | 7 | 21 | 36 | 34 | 47 | 65 | 34 | 105 |
| (125 mg/kg/day) | 8 | 20 | 30 | 21 | 18 | 20 | 20 | — |
| | 9 | 20 | 31 | 44 | 48 | 55 | 46 | 84 |
| | 10 | 27 | 42 | 28 | 35 | 35 | 30 | 66 |
| | 11 | 21 | 50 | 56 | 72 | 64 | 66 | 177 |
| | 12 | 26 | 203 | 247 | 270 | 337 | 361 | 380 |
| X | | 23 | 65 | 72 | 82 | 96 | 93 | 162 |
| S | | 3.2 | 68 | 87 | 94 | 11 | 132 | 129 |
| % of control | | — | — | −27% | −22% | −21% | −15% | −25% |

X = arithmetic mean
S = standard deviation

TABLE 1b

| | | Serum cholesterol [mg/dl] | | | | | | |
|---|---|---|---|---|---|---|---|---|
| | | Starting values before start of administration of the preparation | | Values during the administration of the preparation | | Values after discontinuation of the preparation | | |
| Preparation (Dose) | Animal No. | 1st | 11th day of diet | 3rd | 8th day of administration | 4th | 12th | 32nd day of omission |
| PHM-L | 13 | 28 | 38 | 28 | 32 | 39 | 30 | 57 |
| (500 mg/kg/day) | 14 | 24 | 30 | 32 | 31 | 28 | 22 | 54 |
| | 15 | 20 | 31 | 41 | 65 | 57 | 67 | 90 |
| | 16 | 28 | 43 | 42 | 41 | 58 | 64 | 77 |
| | 17 | 28 | 51 | 96 | 71 | 38 | 47 | 100 |
| | 18 | 26 | 174 | 152 | 178 | 170 | 165 | 333 |
| X | | 26 | 61 | 65 | 70 | 65 | 66 | 119 |
| S | | 3.9 | 56 | 49 | 65 | 53 | 52 | 107 |

TABLE 1b-continued

| | | Serum cholesterol [mg/dl] | | | | | |
|---|---|---|---|---|---|---|---|
| | | Starting values before start of administration of the preparation | | Values during the administration of the preparation | | Values after discontinuation of the preparation | |
| Preparation (Dose) | Animal No. | 1st | 11th day of diet | 3rd | 8th day of administration | 4th | 12th | 32nd day of omission |
| % of control | | — | — | −34% | −33% | −47% | −40% | −45% |

X = arithmetic mean
S = standard deviation

We claim:

1. A pharmaceutical composition for administration to a mammal containing a serum cholesterol-level decreasing amount of a polymer which contains one or both of units (I) and (II) as constituents of the base polymer

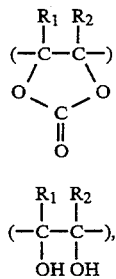

(I)

(II)

in which $R_1$ and $R_2$ independently of one another are hydrogen or a monovalent hydrocarbon radical having up to 8 carbon atoms, and optionally small amounts of further monomer units, the base polymer additionally containing covalently bonded units, grafted onto the base polymer and, optionally, incorporated as end groups thereon, said covalently bonded units being derived from at least one reactant compound of the formula (III)

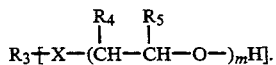

(III)

in which $R_3$, X, $R_4$, $R_5$, m and n have the following meaning:
   $R_3$ is a hydrocarbon radical having 4 to 30 carbon atoms;
   X is one or more of —O—, —NH— and —COO—;
   $R_4$ and $R_5$ independently of one another are hydrogen or a monovalent hydrocarbon radical having 1 to 8 carbon atoms, with the proviso that at least one of $R_4$ and $R_5$ is hydrogen;
   m is an integer from 1 to 40; and
   n is 1, 2, 3, or 4, together with a physiologically acceptable excipient.

2. A pharmaceutical composition as claimed in claim 1, wherein the base polymer contains at least 95% by weight of units of the formula (II), relative to the total amount of units (I) and (II).

3. A pharmaceutical composition as claimed in claim 1, wherein the amount of units according to formula (III) is 1 to 20% by weight, relative to the base polymer.

4. A pharmaceutical composition as claimed in claim 1, wherein $R_1$ and $R_2$ in formula (I) and formula (II) are hydrogen.

5. A pharmaceutical composition as claimed in claim 1, wherein $R_3$ is an alkyl radical having 4 to 30 carbon atoms, X is one or both of —O— and —COO—, $R_4$ and $R_5$ are hydrogen, m is 5 to 35 and n is 1 or 2.

6. A pharmaceutical composition as claimed in claim 1, wherein $R_3$ is an alkyl radical having 12-20 carbon atoms and X is one or both of —O— and —COO—.

7. A pharmaceutical composition as claimed in claim 6, wherein X is —O—.

8. A pharmaceutical composition as claimed in claim 1, which contains a mixture of at least one polymer containing units according to one or both of the formulae (I) and (II) and at least one unit derived from a reactant compound of the formula (III) and at least one crosslinked or uncrosslinked alkylated polyethyleneimine, the starting polyethyleneimine having a molar mass of 10,000 to 10,000,000 and the alkylating agent corresponding to the formula (IV)

R—X     (IV)

in which
   X is chlorine, bromine, iodine, $CH_3—SO_2—O$ or

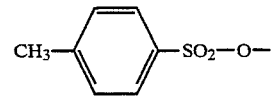

and
   R is a straight-chain, branched or cyclic $C_1$ to $C_{30}$-alkyl radical, which is optionally substituted by a mono- or bicyclic saturated hydrocarbon having 5 to 10 ring carbon atoms or by a phenyl radical, and which in the case of a crosslinked alkylated polyethyleneimine contains as a crosslinking agent an α,ω-dihaloalkane having 2 to 10 carbon atoms or a more highly functionalized haloalkane having 2 to 10 carbon atoms.

9. A pharmaceutical composition as claimed in claim 8, wherein R in formula IV is an optionally bridged cycloalkyl radical having 5 to 30 carbon atoms, which is monocyclic, bicyclic, tricyclic or higher polycyclic.

10. A pharmaceutical composition as claimed in claim 8, wherein R in formula (IV) is cyclopentyl, cyclohexyl, cycloheptyl, cyclooctyl, cyclononyl, cyclodecyl, a bicyclic radical, hydrindanoyl, a bridged radical, or a higher polycyclic radical or a ring system or derivative derived therefrom.

11. A pharmaceutical composition as claimed in claim 1, which contains polyethyleneimines having a molecular weight of 100,000 to 10,000,000.

12. A pharmaceutical composition as claimed in claim 1, which additionally contains one or both of a further bile acid sequestrant and another hypolipidemic agent.

13. A pharmaceutical composition as claimed in claim 1, which contains a bio-inert excipient selected from the group consisting of active carbon, cellulose, chitosan, cyclodextrins, polyvinylpyrrolidone, polyvinyl alcohol and polyacrylic acid derivatives, and optionally one or both of further additives and auxiliaries.

14. A method for decreasing an increased plasma cholesterol level in a patient which comprises administering to said patient a pharmaceutical composition as claimed in claim 12.

15. A process for the production of a pharmaceutical composition as claimed in claim 1, which comprises bringing one or both of the polymer containing units according to the formulae (I) and (II) and at least one unit derived from a reactant compound of the formula (III) and optionally a polyethyleneimine derivative into a suitable form for administration using a physiologically acceptable excipient and, if appropriate, one or both of further additives and auxiliaries.

16. A pharmaceutical composition as claimed in claim 10 wherein the bicyclic radical is decalyl.

17. A pharmaceutical composition as claimed in claim 10 wherein the bridged radical is norbornyl.

18. A pharmaceutical composition as claimed in claim 10 wherein the higher polycyclic radical is cyclopentanoperhydrophenanthrene.

19. A method for decreasing an increased plasma cholesterol level in a patient which comprises administering to said patient a pharmaceutical composition as claimed in claim 8.

20. A method for decreasing an increased plasma cholesterol level in a patient which comprises administering to said patient a pharmaceutical composition as claimed in claim 1.

* * * * *

UNITED STATES PATENT AND TRADEMARK OFFICE
CERTIFICATE OF CORRECTION

PATENT NO. : 5,401,498
DATED : March 28, 1995
INVENTOR(S) : Kurt Kessleler, et al It is certified that error appears in the above-indentified patent and that said Letters Patent is hereby corrected as shown below:

Claim 1, Column 9, Lines 26-29, formula (II) should read

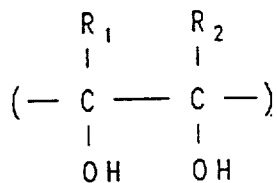

UNITED STATES PATENT AND TRADEMARK OFFICE
CERTIFICATE OF CORRECTION

PATENT NO. : 5,401,498
DATED : March 28, 1995
INVENTOR(S) : Kurt Kessleler, et al It is certified that error appears in the above-indentified patent and that said Letters Patent is hereby corrected as shown below:

Claim 1, Column 9, lines 41-43, formula (III) should read $$R_3 \left[ X-(CH-CH-O-)_m H \right]_n$$

with $R_4$ above the first CH and $R_5$ above the second CH.

Signed and Sealed this

Ninth Day of April, 1996

*Attest:*

BRUCE LEHMAN

*Attesting Officer*     Commissioner of Patents and Trademarks